United States Patent [19]

Harkins et al.

[11] Patent Number: 4,553,687
[45] Date of Patent: Nov. 19, 1985

[54] NEEDLE BREAKING AND STORAGE DEVICE

[76] Inventors: Desira Harkins, 2854 Harmony Pl., La Crescenta, Calif. 91214; Farid MuAddi, 370 Fairview, Arcadia, Calif. 91006

[21] Appl. No.: 431,682

[22] Filed: Jan. 13, 1983

[51] Int. Cl.⁴ ............................................... B26F 3/00
[52] U.S. Cl. ........................................ 225/93; 241/99
[58] Field of Search ....................... 225/93, 1; 83/580; 241/99

[56] References Cited

U.S. PATENT DOCUMENTS

| | | | |
|---|---|---|---|
| 2,488,956 | 11/1949 | Yeskett | 225/96.5 |
| 3,404,593 | 10/1968 | Arcarese et al. | 241/99 X |
| 3,796,359 | 3/1974 | Dick | 225/93 |
| 3,851,555 | 12/1974 | Eldridge et al. | 83/580 X |
| 3,893,608 | 7/1975 | Koenig | 225/93 X |
| 4,275,628 | 6/1981 | Greenhouse | 83/580 X |
| 4,404,881 | 9/1983 | Hanifl | 83/580 X |

Primary Examiner—Frank T. Yost
Attorney, Agent, or Firm—Spensley Horn Jubas & Lubitz

[57] ABSTRACT

A device for facilitating the destruction and storage for disposal of used hypodermic needles and for the destruction and storage of parts of disposable hypodermic syringes is disclosed. The device includes a closed compartment with an aperture in one wall for receiving a hypodermic needle and permitting it to be severed and to fall into a storage receptacle. Various ways of retaining the severed needle tips in the receptacle are shown, including a magnet and a viscous liquid which partially coats the severed tips. The device also includes a second aperture dimensioned to similarly allow the severance of the tip of a hypodermic syringe and a receptacle for the storage of the severed syringe tips. In one embodiment, the device includes a perforable matrix or spongelike region into which a used needle may be temporarily inserted for short term storage prior to being severed. An arrangement for mounting the device on hospital furniture or equipment is also disclosed.

19 Claims, 10 Drawing Figures

U.S. Patent   Nov. 19, 1985   Sheet 1 of 3   4,553,687
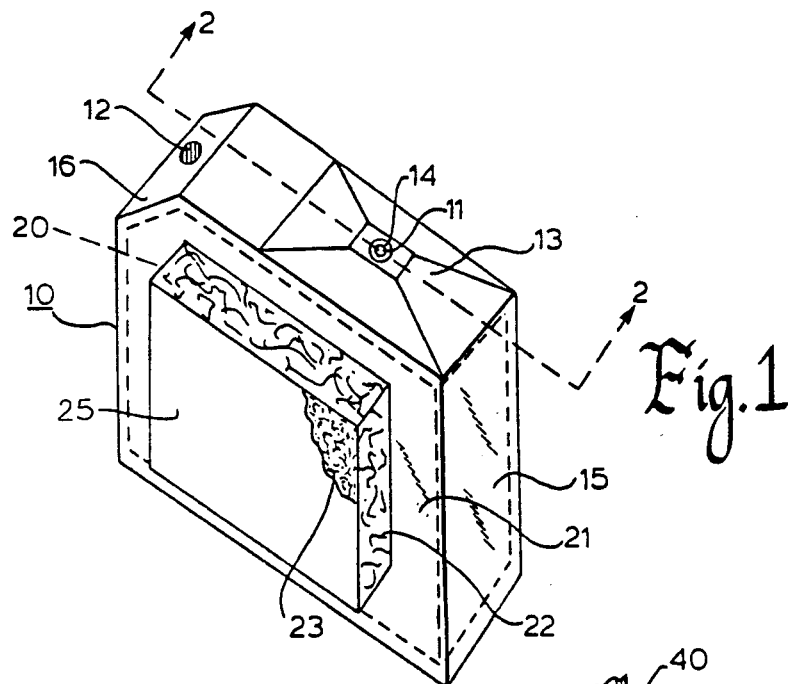
Fig.1
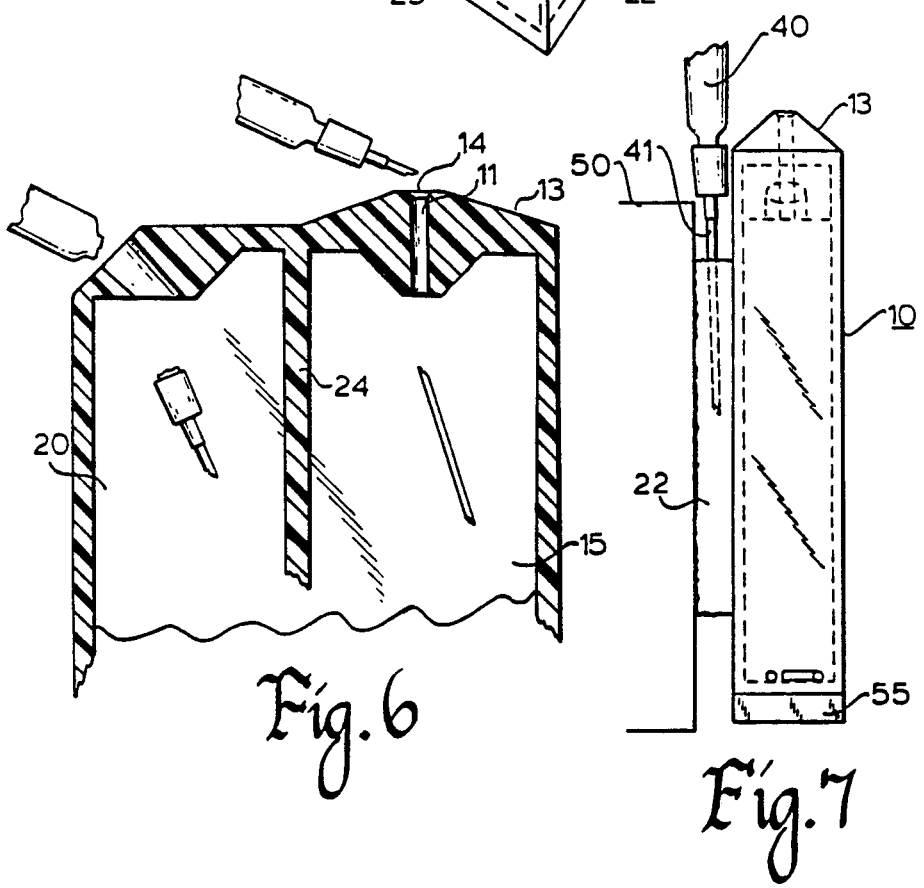
Fig.6
Fig.7

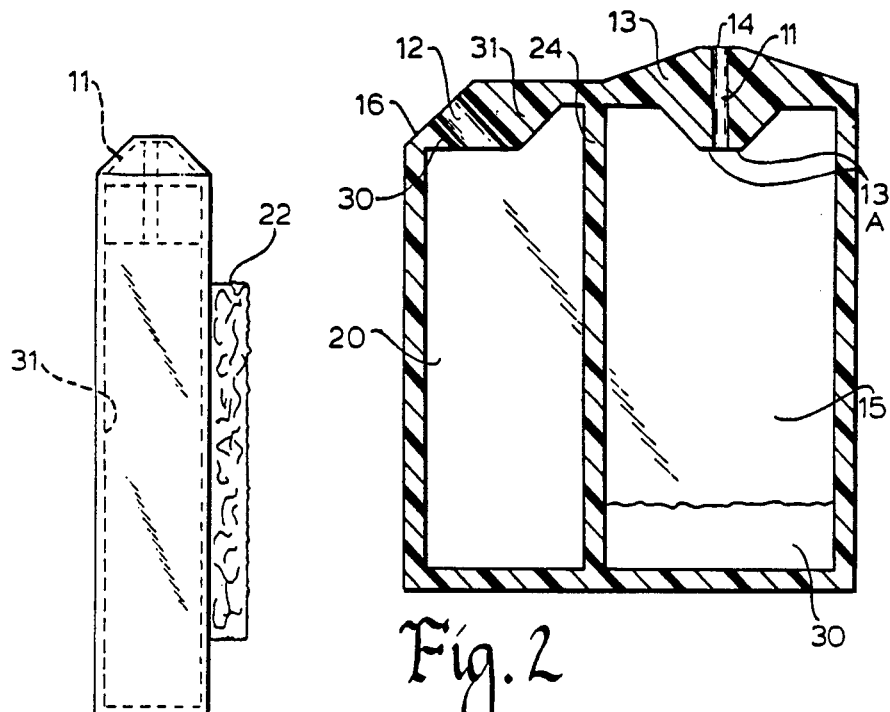
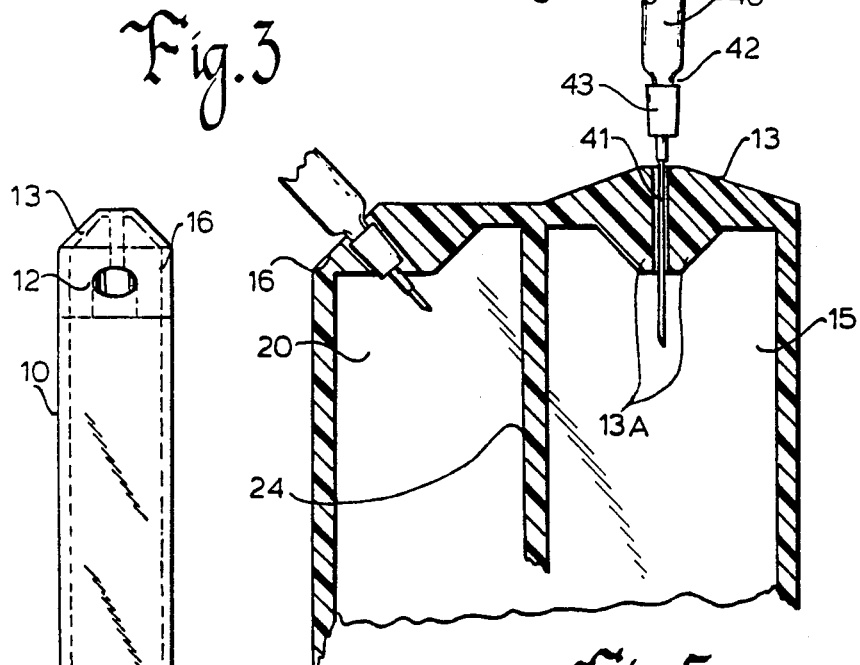

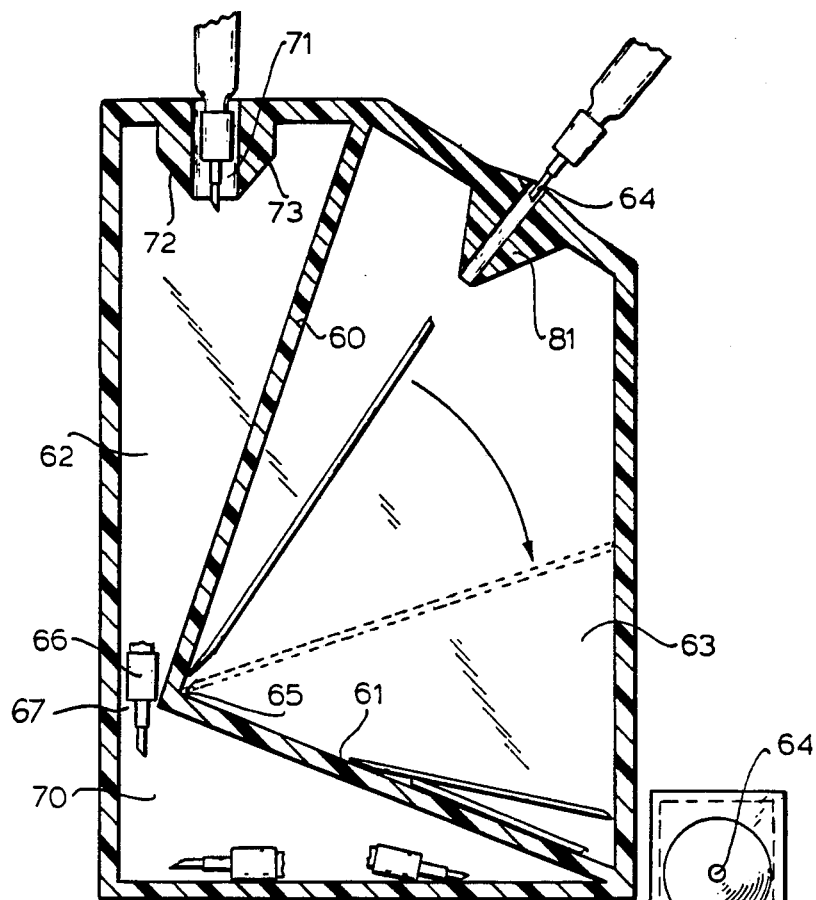
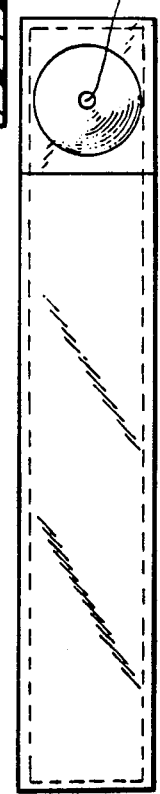
Fig. 8
Fig. 9
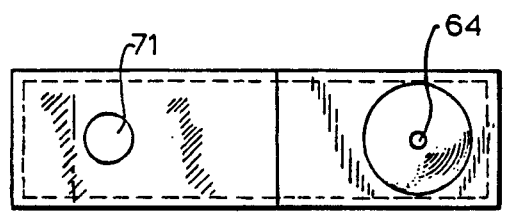
Fig. 10

NEEDLE BREAKING AND STORAGE DEVICE

BACKGROUND OF THE INVENTION

With the advent of the low cost disposable syringe for human injections, the danger of cross-contamination for patients through faulty sterilization of syringes and needles has virtually been eliminated. Today one needle and one syringe is used one time for one patient. The peace of mind afforded to the patient and professional medical personnel is matched by that of the hospital administration responsible in the past for assuring proper sterilization after use and before the next use.

The advantages of disposable syringes and needles are offset by some existing problems, however. The greatest problem is disposal of the used syringe with the assurance that no one can come in contact with the used device nor reuse either the syringe or needle. In the past this has been accomplished by legal restraints against reuse and requiring the destruction of both the needle and the syringe after use.

The most common approach in the past has been for the medical professional to carry a box of some type into which the used needle and syringe are deposited after manually breaking each. Breakage is usually accomplished by replacing the protective sheath on the needle and by bending the sheath and needle against any available hard surface until the needle breaks. The sheath and broken needle are then removed and deposited in the makeshift box. Next the tip of the syringe is pressed against the same hard surface until it breaks. This method is slow and cumbersome and always runs the risk of the medical professional being jabbed by the needle tip or the broken end. A real danger of infection exists. Where an injection therapist must make hundreds of injections on a single shift, the risk of a possible slip in the destruction step is too great to be allowed.

SUMMARY OF THE INVENTION

Having faced the problems described above and having seen medical professionals with their trusty storage box, we felt that there must be a better way. We also noted that many professionals carry their same collection box until it is convenient to empty the needles. Meanwhile it is a time bomb of infection carrying the needles from many patients accumulated over a period of time and accessible to anyone who might open the box.

We were determined to see that a better way to assure rapid, safe destruction of both the needle and syringe could be accomplished with automatic retrieval of the severed part and storage in a manner which made them inaccessible to anyone. Moreover, we wanted assurance that the professional ran no risk of being jabbed by the needle tip or the broken end. We also wanted assurance that once the needle tip was broken and stored, that the needle tip be restrained from removal from its storage container.

A further requirement of any practical needle and syringe disposal system is that the device be easily transportable, used and disposed of. Each of the foregoing requirements are met by our invention, which, in one embodiment, includes a closed container, for example of molded plastic having a pair of openings in one wall thereof. One of the openings is dimensioned to receive a hypodermic needle with the majority of its length extending into the container. The edge of the first opening defines a fulcrum point for bending the needle until it breaks. Sufficient clearance is provided in the first opening so that the needle may fall by its own weight into the container. Preferably some needle tip restraining means is provided in the chamber to prevent the needle tip from reemerging from the first opening.

The container of our invention also includes a second opening which is dimensioned to receive the tip of a syringe including any shank of a needle to allow the tip of the syringe to be broken in a similar manner to the breaking of the needle. The syringe tip may be similarly stored in the container for disposal. A separate chamber for storage of the syringe tip is preferred. Mounting means for the container is provided including a foam plastic pad suitable for acting as a temporary protective storage place for used syringes prior to needle severing.

Suitable means is provided to hold the severed needle tip once it enters the chamber. In one embodiment a viscous liquid is used. In another embodiment, a magnet used principally for mounting the container on metal surfaces also seems to hold severed needle tight by magnetic attraction.

BRIEF DESCRIPTION OF THE DRAWINGS

The invention may be more clearly understood from the following detailed description and by reference to the drawings in which:

FIG. 1 is a perspective drawing of one embodiment of this invention:

FIG. 2 is a vertical sectional view of the device of FIG. 1 taken along line 2—2 of FIG. 1;

FIG. 3 is a left side elevational view thereof;

FIG. 4 is a right side elevational view thereof;

FIGS. 5 and 6 are fragmentary vertical sectional views of the embodiment of FIG. 1 showing the device and a syringe as used to break needles and syringes;

FIG. 7 is a right side elevational view of the device of this invention shown in use as a temporary storage position for a syringe after use and illustrates as well a magnetic form of mounting of the device of this invention;

FIG. 8 is a vertical sectional view of an alternate embodiment of this invention;

FIG. 9 is a right side view thereof; and

FIG. 10 is a top view thereof.

DETAILED DESCRIPTION OF THIS INVENTION

Now referring to FIG. 1, a container 10 in accordance with this invention is shown. It is preferably a molded plastic box of a material such as polystyrene, either clear or opaque as may be desired. The container 10 is closed except for a pair of openings 11 and 12, shown in the top region. Opening 11, the smaller of the two is located in the truncated top of a pyramid shaped region 13 and may include a slightly tapered guide recess 14. The opening 11 itself is preferably between 1/16 and 3/32 in. in diameter, sufficient to receive conventional hypodermic needles. The opening 11 is preferably vertical in order to facilitate the severed end of the needle falling into the chamber 15 to which the opening 11 communicates. The truncated pyramid region 13 serves as a fulcrum against which the used needle of a disposable syringe is bent to sever it at its base region when the syringe is placed needle downward into the recess 14.

The opening 12 is preferably located at a corner cutoff region 16 and extends angularly into a second chamber 20 within the container 10. The opening 12 is larger in diameter than opening 11 and is dimensioned to receive the base or shank of the needle left after the tip has been severed in the opening 11. The angular portion 16 also acts as a fulcrum for the severing of the syringe tip.

On the adjacent or near face 21 of the container 10, an adhesive faced foam pad 22 may be seen. The pad 22 is secured to the face 21 by an adhesive on its inner face and has an adhesive coating 23 on its outer face for attachment to any suitable surface such as an injection therapist's tray or cart. An outer protective cover 25 is present on the container as received and is peeled off to expose the adhesive 23 at the time that the container is intended to be used. The adhesive pad 22 allows the therapist to mount the container 10 at any convenient location and to hold it there with a degree of resilience. The therapist need use only one hand in severing a needle or at most uses the second hand only to steady the container 10 when attached. The shape of the container 10 being rectangular, approximately 4" by 3" by ¾ in. (10.2 by 7.6 by 1.9 cm.) is convenient for being held by the hand as well during needle and syringe tip severing.

The internal arrangement of the container 10 of FIG. 1 is more apparent by reference to FIG. 2 which shows the container to include an internal wall 24 which defines the two chambers 15 and 20. The pyramid portion 13 has its counterpart 13A on the interior of chamber 15 to add strength to the wall 26 in the needle breaking region. The opening 12 is located at a corner region 16 and surrounded by wall thickening reinforcements 30 and 31 as well.

It is desirable that once a needle or syringe tip enters its respective chamber 15 or 20, that it not be allowed to emerge. This is accomplished and virtually assured by two cooperating features of our invention. First, the internal boss or pyramid 13A tend to divert any needles away from the opening 11 if the container 10 is inverted or if shook. This action is just the opposite of the guide recess 14 which aids in the needle entering the opening 11. In addition to the boss 13A, in resisting removal of any needle from the chamber 15, the chamber 15 contains an adhesive material which captures any needle which reaches it. Virtually any non-hardening adhesive or viscous liquid within the chamber 15 will do. An uncured polyesther resin is of sufficient viscosity to coat and hold needles which reach the small pool 30 located at the bottom of the chamber 15. We have also found that double sided adhesive tape bonded to an interior wall of the chamber 15 will capture needle tips and hold them securely once they enter the chamber. We have illustrated this feature in FIG. 3 where double sided tape strip 31 may be seen through the transparent wall of the chamber 10.

The chamber 20 may also include similar adhesive materials for retaining syringe tips once they enter the chamber 20.

The normal use of the device of our invention is best illustrated in FIGS. 5 and 6 in which a disposable syringe 40 is positioned with its needle 41 in the opening 11. The syringe 40 includes a tip 42 which is inserted in the sleeve portion 43 of the needle. The needle 41 is easily broken by pivotal movement around the fulcrum 13 as shown in FIG. 6. The needle may require one or two reverse bends to be severed at which time it will fall into chamber 15 and be captured. The syringe is then transferred to the opening 12 which accomodates the sleeve or hub portion 43 of the needle 41. Again a pivotal movement of the syringe body 40 will cause the tip portion 42 to break and the tip 42 and sleeve portion 43 of the needle fall into the chamber 16. This is illustrated in FIG. 5. The body of the syringe may then be disposed of in conventional waste collection apparatus without fear of reuse or injury from needle remnants.

FIG. 7 illustrates one further feature of this invention resulting from a constant need of the professional providing injections to hospital patients. Often, immediately following an injection, the therapist must devote attention to repositioning the patient or other patient needs and the syringe must be temporarily placed out of the way but in a safe, non-contaminating location. The foam pad 22 of this invention fills that need. The therapist need only drive the needle into the pad from the top or any side where its end is retained and protected from accidental contact. The pad is of sufficient size to insure that most needles will not emerge from the opposite side if inserted to the sleeve portion. As illustrated in FIG. 7, the container of this invention is secured to the side of a cart or tray 50. In such a case, the syringe extends between the wall of the container 10 and the cart or tray 50 and is further protected from contact by these two surfaces.

As soon as the therapist has completed his required duties with the patient, the syringe and needle may be withdrawn from the pad 22 and the needle and syringe broken in the manner described above.

FIG. 6 further discloses an alternate means of mounting the container 10 of this invention which also results in improved retention of severed needle tips.

In FIG. 7, the container 10 carries on one surface, e.g. the bottom surface, a magnet 55 which is secured in place by suitable means such as an adhesive. The magnet is useful to position the container 10 on ferrous tables or trays. Although stainless steel commonly used in hospitals is only slightly ferromagnetic, it exhibits sufficient attraction to the magnet to hold the container in place. Thus, in the embodiment of FIG. 7, the container 10 may be held in place either by adhesion to pad 22 or by magnet 55. By placing the magnet 55 on a wall defining the chamber 15, its magnetic attraction further aids in holding the somewhat ferromagnetic severed needle tips in place and prevents their exiting from entrance opening 11.

Now referring to FIG. 8, a further alternate embodiment of this invention may be seen which includes internal walls which acts as baffles to minimize the possibility of any severed needles or any stylettes severed from syringes escaping from the container. FIG. 8 shows this alternate embodiment in vertical section with continuous inner wall 60 in an L shape with an adjoining wall 61. Wall 60 and 61 separate the two compartments 62 and 63 from each other. Wall 60 has a length of approximately 4 inches whereby a needle as long as 3 to 3-½ inches, if severed, can extend through the opening 64 and drop to the bottom of the severed needle storage place without interference with either wall 60 or 61 before or after it is severed. The wall 60 and its adjoining corner 65 form with wall 61 provides a constriction 67 in the compartment 62. This constriction 67 is wide enough to allow a needle hub to pass through from compartment 62 to the lower storage compartment 70. Once a needle hub 66 passes the constriction 67 it is difficult for it to return through the constriction 67 and through the severing. Even if a needle hub passes back through the constriction 67 the tapered walls 72 and 73 tend to divert the needle hub away from opening 71.

The chamber 63 can accomodate short fine needles which may be ½ to 1 inch long to the longer 3 to 3½ inch stylettes. The wall 61 acts as a floor for the shorter needles to generally rest on. If the device is overturned for any reason the small needles will tend to fall aligned at right angles to the opening 64 and, therefore, assume difficulty in exiting through opening 64. The tapered walls 80 and 81 add to the diversion capability of the assembly.

FIG. 9 and 10 show the side and top view of the assembly of FIG. 8 with the relative positioning of the openings 64 and 71 clearly visible.

Relative dimensions which we have found to be satisfactory are as follows
Overall height, 5 inches (12.7 cm)
Height of lower wall, 4 inches (10.2 cm)
Opening 64, ⅛ inch diameter (0.3 cm)
Length of wall 60, approximately 4 inches (10.2 cm)
Constriction 66, 3/16 inch (0.5 cm)
Opening 71, ⅜" diameter (0.97 cm)
Width of base of box, 3¼ inch (8.3 cm)
Depth of box, ¾ inch (1.9 cm)
Molded Polystyrene is a suitable material for this device.

The containers of this invention are designed for use over a limited period of time such as a single shift of a hospital by a single therapist and they are then destroyed. Destruction is relatively simple. Heating to the softening temperature of the container 10 results in the collapse of the container 10 about the needles and tips fusing the entire mass into a body of plastic material encasing the needle tips. High temperature incineration will cause full decomposition of the container 10 and its adjunct parts such as the pad and melting of the needle tips beyond danger. Although not recommended in place of incineration or mere melting, the container may be carefully disposed of with other disposable waste by other methods found acceptable by relevant safety standards. In any event, the therapist now has a tool to provide rapid and responsible destruction and disposal of hypodermic needles and destruction of disposable syringes.

The foregoing description and the embodiments shown are merely illustrative of this invention and are not to be considered as limiting. The invention is instead defined by the following claims and their equivalents.

We claim:

1. A hypodermic needle breaking and storage device comprising:
    a housing including a cavity for retention of severed hypodermic needles;
    an opening in said housing for receiving the end of a hypodermic needle, said opening having a fixed diameter;
    said housing including a surface against which said needle may be bent when in said opening to fracture said needle and separate the tip region from the remainder of the needle, and an internal surface surrounding the opening in the cavity, that internal surface being shaped and arranged to direct severed needle tips away from said opening;
    said opening communicating with said cavity within the housing whereby the severed tip region of the needle may fall into said cavity after having been severed for retention therein.

2. The combination in accordance with claim 1 in which said housing defines a second opening dimensioned to receive a portion of a hypodermic syringe for fracturing said portion of a hypodermic syringe against a wall of said second opening.

3. The combination in accordance with claim 1 wherein said surface constitutes the edge of said housing defining the outermost extremity of said opening.

4. The combination in accordance with claim 1 wherein said opening is located in an upper portion of said housing whereby the severed tip may fall by gravity into the said cavity.

5. The combination in accordance with claim 4 wherein said opening is located at an elevated portion of the surrounding portions of said housing whereby the needle may be bent to at least 90 degrees while being severed.

6. The combination in accordance with claim 1 including means within said cavity for retaining severed needle tips within said cavity.

7. The combination in accordance with claim 6 wherein said retaining means comprises a viscous liquid capable of coating needle tips.

8. The combination in accordance with claim 6 wherein said retaining means comprises an adhesive material on at least one wall of said cavity.

9. The combination in accordance with claim 6 wherein said retaining means comprises magnetic means providing magnetic attraction in said cavity to attract needle tips to a region away from said opening.

10. The combination in accordance with claim 1 including needle perforable material secured to said housing for temporarily receiving the point of said needle prior to breaking.

11. The combination in accordance with claim 10 wherein said needle perforable material comprises a foam pad secured to said housing.

12. The combination in accordance with claim 2 wherein said housing includes a second cavity communicating with said second opening for storing severed portions of said hypodermic syringe.

13. A hypodermic needle syringe destruction and storage device comprising:
    a housing having walls including a pair of openings therein;
    a first of said pair of openings dimensioned to receive the tip of a hypodermic needle, the wall of said housing defining said first opening constituting a fulcrum for severing said needle by bending thereagainst;
    the second of said pair of openings dimensioned to receive a portion of a hypodermic syringe, the wall defining said second of said pair of openings constituting a fulcrum for the severing of said portion of the syringe by bending thereagainst;
    said first and second openings communicating with different cavities within said housing for storing respective needle tips and syringe portions.

14. The combination in accordance with claim 13 including means for retaining said severed tips and syringe parts within the said respective cavities.

15. The combination in accordance with claim 14, wherein said retaining means comprises a viscous fluid within said cavities for coating severed parts therein.

16. The combination in accordance with claim 14 wherein said retaining means comprises adhesive material on a wall of said cavities.

17. The combination in accordance with claim 14 wherein said retaining means comprises a magnet secured to said housing providing magnetic attraction for ferromagnetic parts within said housing, said magnet located away from said openings.

18. The combination in accordance with claim 13 in which said different cavities are defined in part by a common wall.

19. The combination in accordance with claim 18 wherein the walls of said housing define a restricted region of at least one of said cavities for limiting the exiting of severed party therefrom.

* * * * *